(12) United States Patent
Lorenzo et al.

(10) Patent No.: US 8,951,548 B2
(45) Date of Patent: Feb. 10, 2015

(54) ACRYLIC HYDROGELS WITH PENDANT CYCLODEXTRINS, PREPARATION METHOD THEREOF AND USE OF SAME AS RELEASE SYSTEMS AND CONTACT LENS COMPONENTS

(75) Inventors: Carmen Alvarez Lorenzo, Santiago de Compostela (ES); José Fernando Rosa Dos Santos, Santiago de Compostela (ES); Juan José Torres Labandeira, Santiago de Compostela (ES); Angel Concheiro Nine, Santiago de Compostela (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 162 days.

(21) Appl. No.: 13/057,621

(22) PCT Filed: Aug. 4, 2009

(86) PCT No.: PCT/ES2009/070333
§ 371 (c)(1),
(2), (4) Date: Feb. 25, 2011

(87) PCT Pub. No.: WO2010/018293
PCT Pub. Date: Feb. 18, 2010

(65) Prior Publication Data
US 2011/0200661 A1     Aug. 18, 2011

(30) Foreign Application Priority Data

Aug. 6, 2008   (ES) .................................. 200802364

(51) Int. Cl.
*C08F 290/06*     (2006.01)
*A61K 9/00*     (2006.01)
*A61K 9/14*     (2006.01)

(52) U.S. Cl.
USPC ............ 424/429; 424/484; 424/427; 524/558

(58) Field of Classification Search
None
See application file for complete search history.

(56) References Cited

U.S. PATENT DOCUMENTS 3,647,736  A  *  3/1972  Ewell ............................ 523/108
5,357,012  A  *  10/1994  Nussstein et al. .......... 526/238.2

FOREIGN PATENT DOCUMENTS

| JP | 55-75402 | 6/1980 |
| JP | 2004-161942 | 6/2004 |
| JP | 2005-194200 | 7/2005 |
| JP | 2006-514705 | 5/2006 |

OTHER PUBLICATIONS

Liu et al., Biomaterials 26, 2005, 6367-6374.*
Sreenivasan, J. Applied Poly. Sci, 1996, 60, 22445-2249.*

* cited by examiner

*Primary Examiner* — Kyle Purdy
(74) *Attorney, Agent, or Firm* — Hoffmann & Baron, LLP

(57) ABSTRACT

The invention relates to acrylic hydrogels with pendant cyclodextrins, the preparation and application thereof as release systems and components of contact lenses. The method for obtaining acrylic hydrogels with pendant cyclodextrins is characterized in that the hydrogels are formed by a polymer lattice obtained by polymerization of mono- and bifunctional acrylic or methacrylic monomers and monomers having glycidyl groups in their structure, to which cyclodextrin units are covalently bound once formed; and the use and applications of the compositions in the preparation of contact lenses with the capacity for incorporating drugs, active substances or demulcents useful in the treatment of pathological or physiological conditions, in the production of topical, transdermal or transmucosal release systems for medicinal products or active substances, and in the preparation of cosmetics.

15 Claims, 1 Drawing Sheet

ACRYLIC HYDROGELS WITH PENDANT CYCLODEXTRINS, PREPARATION METHOD THEREOF AND USE OF SAME AS RELEASE SYSTEMS AND CONTACT LENS COMPONENTS

CROSS-REFERENCE TO RELATED APPLICATIONS

This application is the National Stage of International Application No. PCT/ES2009/070333, filed Aug. 4, 2009, which claims the benefit of Spanish Application No. P200802364, filed Aug. 6, 2008, the contents of which are incorporated by reference herein.

FIELD OF THE ART

The present invention relates to acrylic hydrogels with pendant cyclodextrins formed by a polymer lattice, a method for preparing the hydrogels by means of polymerization of mono- and bifunctional acrylic or methacrylic monomers to which cyclodextrin units are covalently bound once formed; and to the use and applications of the compositions in the preparation of contact lenses with the capacity for incorporating drugs, active substances or demulcents, useful in the treatment of pathological or physiological conditions, in the production of topical, transdermal or transmucosal release systems for medicinal products or active substances, and in the preparation of cosmetics.

PRIOR ART

There has been an increasing interest in recent years in using soft contact lenses as reservoirs capable of releasing drugs in a prolonged manner in the precorneal area for the purpose of optimizing ocular bioavailability and making the treatment of acute and chronic pathologies possible by applying simple posological regimens (Alvarez-Lorenzo et al. Am. J. Drug Del. 4: 131-151, 2006).

Attention is also being given to the development of contact lenses containing demulcents to increase comfort during their prolonged use and to palliate dry eye syndrome (Winterton et al., J. Biomed. Mater. Res. B 80: 424-432, 2007; Yañez et al., Eur. J. Pharm. Biopharm. doi:10.1016/j.ejpb.2008.01.023).

In order to carry out to practice the possibility of correcting an eyesight problem and simultaneously pharmacologically treating an eye disease, contact lenses which are capable of incorporating drugs in sufficient amounts for them to be delivered at a suitable rate once inserted into the eye are required. The many approaches that have been developed to provide such qualities to soft contact lenses based on acrylic hydrogels include the immobilization of the drug molecules by means of binding to the polymer structure through labile bonds, the incorporation of a drug to the lens forming part of colloidal structures and the incorporation of the drug to synthesized lenses using functional monomers, in which molecular imprinting techniques may or may not be applied (Alvarez-Lorenzo and Concheiro, Molecularly imprinted materials as advanced excipients for drug delivery systems. In: Biotechnology Annual Review vol. 12, M. R. El-Gewely (editor), Elsevier, Amsterdam 2006, pp. 225-268).

The use of lipophilic cyclodextrin derivatives that are cross-linked by means of hydrosilylation with α,ω-dihydrogen-polydimethylsiloxane (Patent EP 586332) has been proposed for obtaining gas permeable contact lenses formed by cyclodextrin lattices. The cyclodextrins can also be incorporated in intraocular lenses and soft contact lenses forming polyrotaxanes (complexes formed by linear polymers that are inserted in the cavities of several cyclodextrins) and then introducing polymerizable groups in the cyclodextrin units such that they can be subjected to a polymerization process which gives rise to a three-dimensional lattice (Patents JP 2007130386; WO 2006115255; WO 2005095493; WO 2001083566). These methods require the chemical modification of the units of cyclodextrin as a step prior to the formation of the lattice, which complicates the method and may affect the final properties of the lattice.

The incorporation of demulcents, such as polyvinyl alcohol (PVA) or polyvinylpyrrolidone (PVP), has been carried out by adding the free demulcent or the demulcent which has previously formed a macromonomer to the mixture of monomers forming the contact lens prior to polymerization (Bühler et al., Chimia 53:269, 1999; Müller B. U.S. Pat. No. 6,407,145, 2002; Peterson et al., Contact Lens Ant. Eye 29: 127-134, 2006; Winterton et al., J. Biomed. Mater. Res. B 80: 424-432, 2007; Yañez et al., Eur. J. Pharm. Biopharm. doi: 10.1016/j.ejpb.2008.01.023).

The object of the present invention is hydrogels that are capable of effectively incorporating a wide variety of drugs, active ingredients or demulcents by means of forming inclusion complexes with pendant cyclodextrins.

Methods comprising the synthesis of vinyl, acrylic or methacrylic cyclodextrin monomers and the subsequent polymerization of the cyclodextrin monomers with other monomers have been developed to incorporate cyclodextrins in hydrogels or three-dimensional lattices (Lee et al., J. Appl. Polym. Sci. 80: 438-446, 2001; Siemoneit et al., Int. J. Pharm. 312: 66-74, 2006; Rosa dos Santos et al., Acta Biomater. 4: 745-755, 2008). The cyclodextrin monomers are obtained by reacting some of the hydroxyl groups thereof or, if they are cyclodextrin derivatives, the amino groups thereof with monomers having vinyl, acrylic or methacrylic groups. The reaction is difficult to control and it leads to obtaining monomers that contain polymerizable groups in variable proportions and positions. The subsequent polymerization/cross-linking of the monomers gives rise to the formation of lattices in which the units of cyclodextrin are structural links of the chains forming the hydrogel. This generally leads to the lattices having a high rigidity as the polymerizable units of cyclodextrin act as cross-linking agents. In order to obtain flexible hydrogels, it is necessary to incorporate the polymerizable units of cyclodextrin in low proportions, which limits the capacity of the hydrogels to load active substances forming inclusion complexes with the cyclodextrins.

Hydrogels can also be formed from cyclodextrin by direct cross-linking of the cyclodextrins with cross-linking agents containing two or more glycidyl groups in their structure (Patent WO 2006/089993; Rodríguez-Tenreiro et al., Pharm. Res. 23:121-130, 2006; Rodríguez-Tenreiro et al., Eur. J. Pharm. Biopharm. 66: 55-62, 2007; Rodriguez-Tenreiro et al., J. Control. Release 123: 56-66, 2007). This approach also leads to the formation of lattices in which the cyclodextrin units are structural links of the chains which form the hydrogel.

The present invention provides a solution with respect to that known in the prior art which consists of acrylic hydrogels with pendant cyclodextrins having a greater capacity for incorporating drugs, active ingredients or demulcents and a greater capacity for controlling the delivery thereof. These compositions further improve the properties of mechanical strength, flexibility and dimensional stability against hydration.

DESCRIPTION OF THE INVENTION

In the present invention, acrylic or methacrylic chain is understood as a polymer chain resulting from the polymerization of acrylic or methacrylic monomers. Acrylic or methacrylic unit is understood as each monomeric unit forming the polymer chain after the polymerization of acrylic or methacrylic monomers. The monofunctionalized acrylic or methacrylic units are the result of the polymerization of monomers containing a single acrylic or methacrylic group. The bifunctionalized acrylic or methacrylic units are the result of the polymerization of monomers containing two acrylic or methacrylic groups.

One aspect of the invention is aimed at hydrogels in the form of a three-dimensional network, characterized by being formed by cross-linked acrylic or methacrylic chains having alkyl groups to which the cyclodextrins bind by means of an ether bond. To better understand the specification, these hydrogels will be referred to as three-dimensional acrylic hydrogels with pendant cyclodextrins.

The three-dimensional acrylic hydrogels with pendant cyclodextrins, object of this invention, have a high optical clarity and physical and mechanical properties which make them useful for the use thereof as components of medicated soft contact lenses, release systems for drugs, active ingredients or demulcents, or for cosmetics.

In a particular aspect, the acrylic or methacrylic chains of these hydrogels are formed by acrylic or methacrylic units having an alkyl ether group, bifunctionalized acrylic or methacrylic units and monofunctionalized acrylic or methacrylic units.

In a more particular aspect, these three-dimensional acrylic hydrogels with pendant cyclodextrins are characterized in that the proportion of the acrylic or methacrylic units containing an alkyl ether group is preferably between 0.1% and 10% by weight of the hydrogel. In another more particular aspect, the proportion of the bifunctionalized acrylic or methacrylic units is preferably between 0.1% and 10% by weight of the hydrogel.

Another aspect of the invention is aimed at hydrogels in the form of a three-dimensional network characterized by being formed by acrylic or methacrylic chains formed by acrylic or methacrylic units having a glycidyl group, bifunctionalized acrylic or methacrylic units and monofunctionalized acrylic or methacrylic units. These hydrogels are intermediate materials useful in the preparation of three-dimensional acrylic hydrogels with pendant cyclodextrins. To better understand the specification, these hydrogels will be referred to as three-dimensional acrylic hydrogels with glycidyl groups.

Another aspect of the invention is aimed at the preparation of three-dimensional acrylic hydrogels with pendant cyclodextrins by means of a method which comprises immersing a three-dimensional acrylic hydrogel with glycidyl groups in a cyclodextrin solution at alkaline pH.

In a particular aspect, the three-dimensional acrylic hydrogels with glycidyl groups used in the previous method are prepared by means of the polymerization of acrylic or methacrylic monomers having a glycidyl group, monofunctionalized acrylic or methacrylic monomers and bifunctionalized acrylic or methacrylic monomers in the presence of a polymerization primer.

In another aspect, the invention is aimed at hydrogels for their use as a pharmaceutical carrier in the administration of a drug, an active substance or a demulcent.

In a final aspect, the invention is aimed at the use of hydrogels for producing contact lenses which can optionally incorporate a drug, an active substance or a demulcent; to the use for producing topical, transdermal or transmucosal release systems for a drug, an active substance or a demulcent; and to the use for preparing cosmetics.

DETAILED DESCRIPTION OF THE INVENTION

The three-dimensional acrylic hydrogels with pendant cyclodextrins have the capacity for incorporating water in high proportions without being dissolved, giving rise to viscoelastic systems provided with high optical clarity.

Particularly, the cyclodextrins are preferably selected from α-, β- or γ-cyclodextrin, a cyclodextrin formed by more than eight units of α-1,4-glucopyranose, or a linear or branched alkyl, linear or branched hydroxyalkyl, acetyl-, propionyl-, butyryl-, succinyl-, benzoyl-, palmityl-, toluenesulfonyl-, acetyl alkyl, glucosyl-, maltosyl-, carboxymethyl ether-, carboxymethyl alkyl-, phosphate ester-, 3-trimethylammonium-, sulfobutyl ether-cyclodextrin derivative, or a cyclodextrin polymer.

More particularly, the proportion of cyclodextrins is comprised between 1 and 0.2 units of cyclodextrin for each alkyl ether group.

The three-dimensional acrylic hydrogels with pendant cyclodextrins further have the capacity for incorporating a drug, an active substance or a demulcent. These compositions are very suitable for controlling the delivery of drugs, active ingredients or demulcents. The compositions provide different delivery rates depending on their qualitative and quantitative composition and the physicochemical properties of the drug, especially its hydrosolubility and affinity for the cyclodextrin cavity. For a hydrosoluble drug or active substance with an affinity constant for β-cyclodextrin equal to $170 M^{-1}$, typical delivery percentage values are 50% after 2 days, 80% after 8 days and 100% after 24 days.

The compositions which incorporate demulcents are useful for reducing the coefficient of friction of the hydrogels or of the contact lenses.

The method for obtaining three-dimensional acrylic hydrogels with pendant cyclodextrins comprises immersing the three-dimensional acrylic hydrogel with glycidyl groups in a cyclodextrin solution at alkaline pH. The hydroxyl groups of the units of cyclodextrin thus react with the glycidyl groups present in the hydrogel and give rise to ether bonds. If desired, the resulting hydrogels can be washed and optionally dried.

It is an advantageous method since it is not necessary to previously obtain a vinyl, acrylic or methacrylic cyclodextrin monomer having polymerizable groups.

The drug, active substance or demulcent is incorporated into the three-dimensional acrylic hydrogel with pendant cyclodextrins by submerging it in a solution or in a suspension of the drug, the active substance or the demulcent. The drug or the active substance forming inclusion complexes with the cyclodextrins can also be incorporated before the immersion of the three-dimensional acrylic hydrogel with glycidyl groups is carried out.

Three-dimensional acrylic hydrogels with glycidyl groups are obtained by means of a method comprising the polymerization of acrylic or methacrylic monomers having a glycidyl group, monofunctionalized acrylic or methacrylic monomers and bifunctionalized acrylic or methacrylic monomers in the presence of a polymerization primer.

Polymerization can be initiated by means of heating the mixture or by exposing it to ultraviolet-visible radiation.

The polymerization process can be performed in molds of suitable sizes to provide the hydrogels with the shape that is required for their use as components of release systems for drugs, active ingredients or demulcents, or as medicated contact lenses.

The three-dimensional acrylic hydrogels with glycidyl groups are characterized by containing in their structure acrylic or methacrylic units having a glycidyl group, and particularly the monomers which give rise to these units are preferably glycidyl acrylate or glycidyl methacrylate; acrylic or methacrylic units having two acrylic or methacrylic groups in their structure and act as cross-linking agents, and particularly the monomers which give rise to these units are preferably ethylene glycol dimethacrylate, 1,3-butanediol diacrylate, 1,4-butanediol diacrylate, 1,6-hexanediol diacrylate, ethylene glycol diacrylate, fluorescein O,O'-diacrylate, glycerol 1,3-diglycerolate diacrylate, pentaerythritol diacrylate monostearate, 1,6-hexanediol ethoxylate diacrylate, 3-hydroxy-2,2-dimethylpropyl 3-hydroxy-2,2-dimethylpropionate diacrylate, bisphenol A ethoxylate diacrylate, di(ethylene glycol) diacrylate, neopentyl glycol diacrylate, poly (ethylene glycol) diacrylate, poly(propylene glycol) diacrylate, propylene glycol glycerolate diacrylate, tetra(ethylene glycol) diacrylate, 1,3-butanediol dimethacrylate, 1,4-butanediol dimethacrylate, 1,6-hexanediol dimethacrylate, bisphenol A dimethacrylate, diurethane dimethacrylate, ethylene glycol dimethacrylate, fluorescein O,O'-dimethacrylate, glycerol dimethacrylate, bisphenol A ethoxylate dimethacrylate, bisphenol A glycerolate dimethacrylate, di(ethylene glycol) dimethacrylate, poly(ethylene glycol) dimethacrylate, poly(propylene glycol) dimethacrylate, tetraethylene glycol dimethacrylate, tri(ethylene glycol) dimethacrylate, triethylene glycol dimethacrylate, poly(lauryl methacrylate-co-ethylene glycol dimethacrylate), poly (methyl methacrylate-co-ethylene glycol dimethacrylate); acrylic or methacrylic units having an acrylic or methacrylic group in their structure, and particularly the monomers which give rise to these units are preferably hydroxyethyl methacrylate, 1-(tristrimethylsiloxysilylpropyl)-methacrylate, methylmethacrylate, N,N-dimethylacrylamide, N,N-diethylacrylamide, methacrylic acid, acrylic acid, aminopropyl methacrylate, cyclohexyl methacrylate or fluoro-siloxane acrylate.

The proportion of acrylic or methacrylic units having a glycidyl group in their structure is preferably comprised between 0.1 and 10% weight/weight from the total weight of the components of the acrylic lattice; the proportion of bifunctional acrylic or methacrylic units which act as cross-linking agents is preferably comprised between 0.1% and 10% weight/weight; and the proportion of acrylic or methacrylic units having an acrylic or methacrylic group in their structure is preferably comprised between 80% and 99.8% weight/weight.

The excellent biocompatibility of the cyclodextrins and the acrylic lattices leads to the resulting compositions being able to be used as components of biomedical devices or of medicated contact lenses. The method further takes place in conditions that do not compromise the stability of the drugs, active substances or demulcents, and no residues involving environmental contamination hazards are generated during the process.

This all means that the compositions object of the invention can be advantageously used as components of topical, transdermal or transmucosal release systems for drugs or active substances, as components of contact lenses medicated with drugs or active substances or of contact lenses which incorporate demulcents, and as components for cosmetics.

EMBODIMENT

Figure 1:
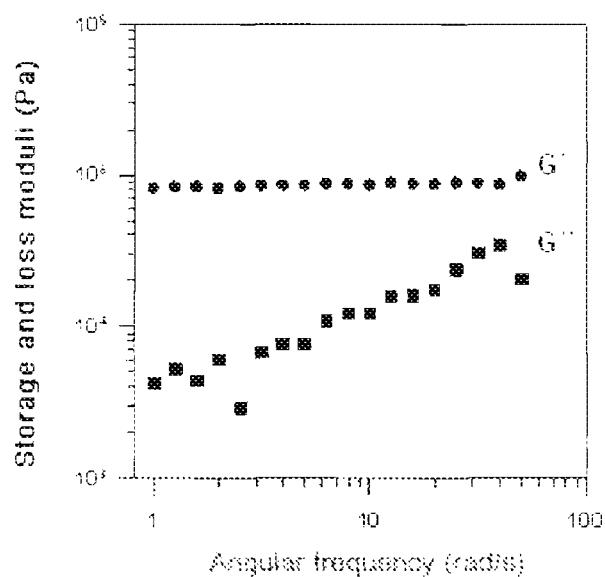
FIG. 1 shows the evolution over time of the values of storage (•) and loss (○) modulus of the acrylic hydrogel with pendant β-cyclodextrin 1 (Table 1).
Figure 2:
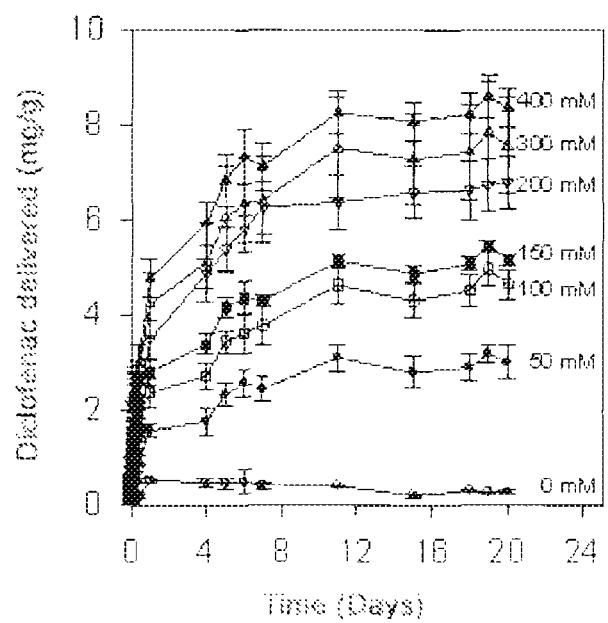
FIG. 2 shows the delivery profiles of diclofenac from the compositions based on acrylic hydrogels with pendant β-cyclodextrin to which the drug was incorporated by immersion in a solution of sodium diclofenac (Table 2). The assay was carried out by introducing each disc into a vial with 10 ml of an aqueous solution of artificial tear fluid at pH 8, prepared with NaCl (6.78 g/L), NaHCO$_3$ (2.18 g/L), KCl (1.38 g/L) and CaCl$_2$.2H$_2$O (0.084 g/L). All the compositions controlled the release process up to 24 days.

Examples showing how acrylic hydrogels with pendant cyclodextrins are obtained, the quantification of the cyclodextrin content and the evaluation of the transparency and mechanical properties of the compositions obtained are included below. Examples for preparing compositions which incorporate drugs and release them in a controlled manner are also included. These examples serve to illustrate, not limit, the invention.

To carry out the preparation of the three-dimensional acrylic hydrogels with pendant cyclodextrin, a cyclodextrin solution with a concentration comprised between 1 and 5% weight/weight is first prepared in a medium formed by sodium chloride 0.5M:dimethylformide 50:50 v/v solution alkalinized with 3% NaOH, using a mechanical or magnetic stirrer and, if necessary, applying ultrasounds. The three-dimensional acrylic hydrogel with glycidyl groups is introduced into this solution such that the weight of the solution is between 10 and 50 times its weight, and the system is maintained at 60-90° C. for 24 hours. Once this time has lapsed, the hydrogels obtained are washed with water or with a 0.9% sodium chloride solution at 60-90° C. or applying an autoclave cycle. They are dried at room temperature and submerged in ethanol for 24 hours, replacing the medium every 8 hours. The washing process is considered to have ended when the absorbance of the washing medium is less than 0.001 in the entire wavelength range comprised between 190 and 800 nm. The washing times are usually comprised between 20 minutes and 1 day. The hydrogels are conserved submerged in aqueous medium or dried by using a vacuum oven or an air flow oven, or by applying lyophilization.

To quantify the pendant cyclodextrin in the three-dimensional acrylic hydrogel with pendant cyclodextrins, the absorption of organic molecules with a high affinity for cyclodextrins (typical organic compounds, TOC), such as indole for α-cyclodextrin, 3-methylbenzoic acid for β-cyclodextrin or Congo red for γ-cyclodextrin can be measured (Fundueanu et al. J. Chromatogr. B 2003; 791:407-419). The final pendant cyclodextrin content is comprised between 1 and 0.2 units of cyclodextrin for each glycidyl group present in the acrylic lattice before the reaction with the cyclodextrins. The conversion of the glycidyl groups into ether bonds can be monitored by infra-red spectrophotometry.

The drug or the active substance is incorporated into the three-dimensional acrylic hydrogel with pendant cyclodextrins by directly immersing the hydrogel in a solution or in a suspension of the drug or active substance at a temperature comprised between 0 and 100° C. and at atmospheric pressure with or without the aid of ultrasounds. The incorporation can also be carried out in an autoclave at a temperature comprised between 100 and 130° C. The drug or the active substance forming inclusion complexes with the cyclodextrins when they are anchored to the polymer lattice can also be incorporated.

The demulcent is incorporated into the acrylic hydrogel with pendant cyclodextrins by directly immersing the hydrogel in a solution of the demulcent at a temperature comprised between 0 and 100° C. and at atmospheric pressure, with or without the aid of ultrasounds. The incorporation can also be carried out in an autoclave at a temperature comprised between 100 and 130° C. Examples of demulcents include certain cellulose derivatives such as carboxymethyl cellulose (CMC), hydroxyethyl cellulose (HEC), hydroxypropyl cellulose (HPC) or methyl cellulose (MC), dextran, gelatin, polyols such as glycerine, polyethylene glycol (PEG), polysorbate 80, propylene glycol, polyvinyl alcohol (PVA) and polyvinylpyrrolidone (PVP, povidone).

The amount of drug, active substance or demulcent that is incorporated into the hydrogel is calculated from the initial and final concentrations of the drug, active substance or demulcent in the solution or the suspension used for incorporating them into the hydrogel.

The compositions obtained can be used to produce contact lenses which incorporate drugs, active substances or demulcents intended for the treatment of pathological or physiological conditions in humans. They can also be used to produce topical, transdermal or transmucosal release systems for drugs or active substances and for preparing cosmetics.

Example 1

Method for Obtaining an Acrylic Hydrogel with α-Cyclodextrin, β-Cyclodextrin, Hydroxypropyl-β-Cyclodextrin, Methyl-β-Cyclodextrin or Pendant γ-Cyclodextrin A hydroxyethyl methacrylate (HEMA) hydrogel was prepared by dissolving 0.0714 ml of ethylene glycol dimethacrylate (EGDMA, 8 mM), 0.074 g of azoisobutyronitrile (AIBN, 10 mM) and 0.245 ml of glycidyl methacrylate (GMA, 300 mM) in 6 ml of HEMA, injecting the mixture into molds formed by glass plates internally covered with a polypropylene sheet and separated by a silicone frame 0.4 mm thick, and heating at 50° C. for 12 hours and at 70° C. for another 24 hours. The hydrogel sheets were submerged in boiling water for 15 minutes to remove the non-reacting monomers and to facilitate cutting discs 10 mm in diameter. The discs were submerged in water for 24 hours, then in 0.9% NaCl for another 24 hours and finally in water for another 24 hours.

The wet discs were submerged in portions of 100 ml of solution of α-cyclodextrin, β-cyclodextrin, hydroxypropyl-β-cyclodextrin, methyl-β-cyclodextrin or γ-cyclodextrin with a concentration of 0.019 M which was prepared by incorporating the corresponding cyclodextrin into a mixture of an aqueous solution of 0.5 M sodium chloride (50 ml) and dimethylformide (50 ml) to which NaOH was added until reaching a concentration of 3%. The system was maintained at 80° C. for 24 hours. The hydrogels were washed with water at 80° C., dried at room temperature, and submerged in ethanol for 24 hours, replacing the medium every 8 hours.

Example 2

Method for Quantifying the Cyclodextrin Content of an Acrylic Hydrogel with β-Cyclodextrin, Hydroxypropyl-β-Cyclodextrin or Pendant Methyl-β-Cyclodextrin To determine the content of β-cyclodextrin, hydroxypropyl-β-cyclodextrin or methyl-β-cyclodextrin in the acrylic hydrogel compositions with β-cyclodextrin, hydroxypropyl-β-cyclodextrin or pendant methyl-β-cyclodextrin obtained in example 1, the following method was applied. Dry discs of each hydrogel submerged in an aqueous solution of 3-methylbenzoic acid (0.5 mg/ml, 10 ml per disc) were maintained for 48 hours in the dark. Once this time had lapsed, the concentration of 3-methylbenzoic acid was spectrophotometrically determined at 281 nm and the total amount of 3-methylbenzoic acid captured by the hydrogel was estimated using the difference with respect to the initial concentration.

The amount of 3-methylbenzoic acid captured as it forms complexes with β-cyclodextrin, hydroxypropyl-β-cyclodextrin or pendant methyl-β-cyclodextrin was estimated by subtracting from the total amount of 3-methylbenzoic acid which the acrylic hydrogel with β-cyclodextrin, hydroxypropyl-3-cyclodextrin or pendant methyl-β-cyclodextrin captured, the amount of 3-methylbenzoic acid captured by an acrylic hydrogel of the same composition without cyclodextrin.

In all of the cases, the molar ratio of pendant cyclodextrin/glycidyl was within the range of 1-0.33.

Example 3

Method for Obtaining Acrylic Hydrogels with Different Pendant β-Cyclodextrin Contents and Evaluation of the Mechanical and Optical Properties Thereof Hydrogels of hydroxyethyl methacrylate (HEMA) were prepared by dissolving 0.0714 ml of ethylene glycol dimethacrylate (EGDMA, 8 mM), 0.074 g of azoisobutyronitrile (AIBN, 10 mM) and volumes of glycidyl methacrylate (GMA) comprised between 0.041 and 0.327 ml (50 to 400 mM) in 6 ml of HEMA, injecting the mixtures in molds formed by glass plates internally coated with polypropylene sheets and separated by a silicone frame 0.4 mm thick, and heating at 50° C. for 12 hours and at 70° C. for another 24 hours. The hydrogel sheets were submerged in boiling water for 15 minutes to remove the non-reacting monomers and to facilitate cutting discs 10 mm in diameter. The discs were submerged in water for 24 hours, then in 0.9% NaCl for another 24 hours and finally in water for another 24 hours.

The wet Discs (6 discs for each proportion of GMA) were submerged in portions of 100 ml of solution of β-cyclodextrin with a concentration of 0.019 M, prepared by incorporating β-cyclodextrin into a mixture of aqueous solution of 0.5 M sodium chloride (50 ml) and dimethylformide (50 ml) to which NaOH was added until reaching a concentration of 3%, and they were maintained at 80° C. for 24 hours The hydrogels were washed with water at 80° C., dried at room temperature, and were maintained submerged in ethanol for 24 hours, replacing the ethanol every 8 hours. Finally, they were dried in an oven at 40° C.

The results of the determination of the β-cyclodextrin content obtained by applying the method described in example 2 are included in Table 1. The glass transition temperature, Tg, was determined by differential scanning calorimetry (DSC Q100, TA Instruments, USA) by subjecting 10 mg of each acrylic hydrogel with pendant β-cyclodextrin to a heating ramp from 25° C. to 300° C. The Tg values were estimated as the temperature corresponding to the mid point of the base line change. FIG. 1 shows the rheometric profile of the hydrogel 1 hydrated in water recorded in a TA Instruments AR-1000N rheometer, applying a deformation of 0.5% at room temperature.

TABLE 1

Composition and glass transition temperature of acrylic hydrogels with pendant β-cyclodextrin (βCD) produced as described in Example 3

| Hydrogel | Proportion of GMA used in the synthesis of the hydrogel (mM) | GMA (mmol/g) | Pendant βCD content (mmol/g) | GMA/βCD molar ratio | Tg (° C.) |
|---|---|---|---|---|---|
| 1 | 400 | 0.364 | 0.177 | 2.33 | 110 |
| 2 | 300 | 0.276 | 0.130 | 2.38 | 109 |
| 3 | 200 | 0.187 | 0.086 | 2.38 | 111 |
| 4 | 150 | 0.141 | 0.075 | 2.05 | 110 |
| 5 | 100 | 0.095 | 0.054 | 1.92 | 109 |
| 6 | 50 | 0.048 | 0.016 | 2.96 | 109 |
| 7 | 0 | 0 | 0 | — | 110 |

Example 4

Method for Obtaining Acrylic Hydrogels with Different Pendant β-Cyclodextrin Contents which Incorporate Sodium Diclofenac and Deliver it in a Controlled Manner Hydrogels of hydroxyethyl methacrylate with different pendant β-cyclodextrin contents (Table 1) were cut into discs 8 mm in diameter and were introduced into vials containing 10 mL of sodium diclofenac (80 mg/L) solution which were maintained at 25° C. Once 4 days had lapsed, the incorporated diclofenac was quantified using the differences between the amount of diclofenac present in the solution at the beginning and at the end of the assay (spectrophotometric titration at 276 nm, Agilent 8453, Germany). By way of example, Table 2 shows the diclofenac contents of hydrogel discs with different compositions. The hydrogels with the highest pendant β-cyclodextrin content captured an amount of diclofenac 28 times greater than that captured by the acrylic hydrogels of the same composition without pendant β-cyclodextrin.

TABLE 2

Amount of diclofenac captured by hydrogels with pendant β-cyclodextrin with different β-cyclodextrin contents.

| Hydrogel | Pendant β-cyclodextrin content (mmol/g) | Incorporated diclofenac (mg/g) |
|---|---|---|
| 1 | 0.177 | 8.6 |
| 2 | 0.130 | 7.7 |
| 3 | 0.086 | 6.4 |
| 4 | 0.075 | 4.8 |
| 5 | 0.054 | 2.6 |
| 6 | 0.016 | 2.3 |
| 7 | 0 | 0.3 |

The invention claimed is:

1. A contact lens for the release of drugs, active substances or demulcents comprising a hydrogel in the form of a three-dimensional network wherein the hydrogel is formed by cross-linked acrylic or methacrylic chains having alkyl groups to which cyclodextrins are bound by means of an ether bond, wherein the acrylic or methacrylic chains are formed from acrylic or methacrylic units having an alkyl ether group and wherein the proportion of the acrylic or methacrylic units containing an alkyl ether group is between 0.1% and 10% by weight of the hydrogel.

2. The contact lens according to claim 1, wherein the cyclodextrin is selected from α-, β- or γ-cyclodextrin, a cyclodextrin formed by more than eight units of α-1,4-glucopyranose, or a linear or branched alkyl, linear or branched hydroxyalkyl, acetyl-, propionyl-butyryl-, succinyl-, benzoyl-, palmityl-, toluenesulfonyl-, acetyl alkyl, glucosyl-, maltosyl-, carboxymethyl ether-, carboxymethyl alkyl-, phosphate ester-, 3-trimethylammonium-, sulfobutyl ether-cyclodextrin derivative, or a cyclodextrin polymer.

3. The contact lens according to claim 1, characterized in that the proportion of cyclodextrins is comprised between 1 and 0.2 units of cyclodextrin for each alkyl ether group.

4. The contact lens according to claim 1, comprising a drug, an active substance, or a demulcent.

5. The contact lens according to claim 1, wherein the cyclodextrins are forming inclusion complexes with drugs, active substances, or demulcents.

6. The contact lens according to claim 1, wherein the acrylic or methacrylic chains further comprise: bifunctionalized acrylic or methacrylic units and monofunctionalized acrylic or methacrylic units.

7. The contact lens according to claim 6, wherein the proportion of the bifunctionalized acrylic or methacrylic units is between 0.1% and 10% by weight of the hydrogel.

8. The contact lens according to claim 6, wherein the bifunctionalized acrylic or methacrylic units are selected from ethylene glycol dimethacrylate, 1,3butanediol diacrylate, 1,4-butanediol diacrylate, 1,6hexanediol diacrylate, ethylene glycol diacrylate, fluorescein O,O'-diacrylate, glycerol 1,3-diglycerolate diacrylate, pentaerythritol diacrylate monostearate, 1,6-hexanediol ethoxylate diacrylate, 3-hydroxy-2,2-dimethylpropyl 3-hydroxy-2,2-dimethylpropionate diacrylate, bisphenol A ethoxylate diacrylate, di(ethylene glycol) diacrylate, neopentyl glycol diacrylate, poly(ethylene glycol) diacrylate, polypropylene glycol) diacrylate, propylene glycol glycerolate diacrylate, tetra(ethylene glycol) diacrylate, 1,3-butanediol dimethacrylate, 1,4-butanediol dimethacrylate, 1,6-hexanediol dimethacrylate, bisphenol A dimethacrylate, diurethane dimethacrylate, ethylene glycol dimethacrylate, fluorescein O,O'-dimethacrylate, glycerol dimethacrylate, bisphenol A ethoxylate dimethacrylate, bisphenol A glycerolate dimethacrylate, di(ethylene glycol) dimethacrylate, poly(ethylene glycol) dimethacrylate, poly(propylene glycol) dimethacrylate, tetraethylene glycol dimethacrylate, tri(ethylene glycol) dimethacrylate, triethylene glycol dimethacrylate, poly(lauryl methacrylate-co-ethylene glycol dimethacrylate) and poly(methyl methacrylate-co-ethylene glycol dimethacrylate).

9. A method for obtaining the contact lens of claim 1, comprising reacting acrylic or methacrylic chains formed from acrylic or methacrylic units having an alkyl ether group with a cyclodextrin solution under alkaline conditions, whereby an ether bond is formed between the alkyl group of the polymer and the cyclodextrin.

10. The method according to claim 9, wherein the cyclodextrin solution has a concentration between 1% and 5% by weight.

11. The method according to claim 9, wherein the cyclodextrin is preferably selected from α-, β- or γ- cyclodextrin, a cyclodextrin formed by more than eight units of α-1,4-glucopyranose, or a linear or branched alkyl, linear or branched hydroxyalkyl, acetyl-, propionyl-, butyryl-, succinyl-, benzoyl-, palmityl-, toluenesulfonyl-, acetyl alkyl, glucosyl-, maltosyl-, carboxymethyl ether-, carboxymethyl alkyl-, phosphate ester-, 3-trimethylammonium-, sulfobutyl ether-cyclodextrin derivative, or a cyclodextrin polymer.

12. The method according to claim 9, wherein the immersion of the hydrogel in a cyclodextrin solution is maintained at a temperature between 60 and 90° C.

13. The method according to claim 9, wherein a drug or an active substance is further incorporated into the hydrogel, preferably by directly immersing the hydrogel in a solution or in a suspension of the drug or active substance at a temperature comprised between 0 and 100° C. and at atmospheric pressure, or in an autoclave at a temperature comprised between 100 and 130° C.

14. The method according to claim 9, wherein the acrylic or methacrylic units having an alkyl ether group are acrylic or methacrylic units having a glycidyl group.

15. The contact lens according to claim 6, wherein the monofunctionalized acrylic or methacrylic units are hydroxyethyl methacrylate, 1-(tristrimethylsiloxysilylpropyl)-methacrylate, methylmethacrylate, N,N-dimethylacrylamide, N,N-diethylacrylamide, methacrylic acid, acrylic acid, aminopropyl methacrylate, cyclohexyl methacrylate or fluorosiloxane acrylate.

* * * * *